United States Patent
Gammons

(10) Patent No.: US 8,512,263 B2
(45) Date of Patent: Aug. 20, 2013

(54) DISPOSABLE PORTABLE THERAPY DEVICE

(75) Inventor: Scott Gammons, Loudon, TN (US)

(73) Assignee: Adroit Medical Systems, Inc., Loudon, TN (US)

( * ) Notice: Subject to any disclaimer, the term of this patent is extended or adjusted under 35 U.S.C. 154(b) by 853 days.

(21) Appl. No.: 12/605,650

(22) Filed: Oct. 26, 2009

(65) Prior Publication Data

US 2011/0098610 A1  Apr. 28, 2011

(51) Int. Cl.
- *A61H 1/00* (2006.01)
- *A61H 1/02* (2006.01)
- *A61H 5/00* (2006.01)
- *A61F 7/00* (2006.01)

(52) U.S. Cl.
USPC .............................. 601/15; 607/104; 607/108

(58) Field of Classification Search
USPC .................. 601/15; 607/81, 85–87, 96, 104, 607/108–112, 114; 220/592.2, 592.23, 592.25; 206/523, 702, 728
See application file for complete search history.

(56) References Cited

U.S. PATENT DOCUMENTS

| | | | | |
|---|---|---|---|---|
| 2,515,709 A | * | 7/1950 | Heard et al. | 220/23.87 |
| 2,611,851 A | | 9/1952 | Lott | |
| 2,828,903 A | | 4/1958 | Adkins | |
| 2,839,654 A | | 6/1958 | Jones et al. | |
| 3,472,455 A | * | 10/1969 | Priest et al. | 239/135 |
| 3,536,248 A | | 10/1970 | Malmo et al. | |
| 3,627,116 A | * | 12/1971 | Cooper | 206/497 |
| 4,037,081 A | * | 7/1977 | Aldridge et al. | 219/387 |
| 4,257,415 A | * | 3/1981 | Rubin | 128/200.21 |
| 4,267,700 A | * | 5/1981 | Minter | 62/70 |
| 4,320,856 A | | 3/1982 | Stewart et al. | |
| 4,498,312 A | * | 2/1985 | Schlosser | 62/457.2 |
| 4,813,536 A | * | 3/1989 | Willis | 206/765 |
| 4,844,072 A | | 7/1989 | French et al. | |
| 4,860,555 A | * | 8/1989 | Bishop et al. | 62/376 |
| 5,057,282 A | | 10/1991 | Linder | |
| D321,915 S | * | 11/1991 | Urbanski | D14/454 |
| 5,062,527 A | | 11/1991 | Westerman | |
| 5,241,951 A | * | 9/1993 | Mason et al. | 607/104 |
| 5,245,221 A | | 9/1993 | Schmidt et al. | |
| D345,802 S | | 4/1994 | Mason et al. | |

(Continued)

OTHER PUBLICATIONS

International Search Report and Written Opinion for PCT/US2010/053912, WO 2011/056493, dated Dec. 22, 2010, 19 pages.

*Primary Examiner* — Justine Yu
*Assistant Examiner* — Raymond G Chen
(74) *Attorney, Agent, or Firm* — Knox Patents; Thomas A. Kulaga

(57) ABSTRACT

Apparatus for a disposable, portable thermal therapy device that is self-contained for shipping as a single unit to a patient. The therapy device has a shipping configuration that presents a single, self-contained durable container. The container includes an insert that defines a compartment between the insert and the container. The compartment storing various electrical components. The insert has a cavity that contains a pump and stores a thermal pad and associated fluid lines. The therapy device has a deployed configuration in which the power connector, the control unit, and the thermal pad are extended from the interior of the container. In one embodiment, the insert is a solid insulating material that has a configuration suitable for nesting the inserts for shipping. In another embodiment, the insert is a planar material folded into a basket shape. Insulation is provided by the gap between the insert and the containing box.

26 Claims, 4 Drawing Sheets

(56) References Cited

U.S. PATENT DOCUMENTS

| | | | |
|---|---|---|---|
| 5,330,519 A | 7/1994 | Mason et al. | |
| 5,336,249 A | 8/1994 | Mahawili | |
| 5,447,252 A * | 9/1995 | Ward | 220/756 |
| 5,476,489 A | 12/1995 | Koewler | |
| 5,486,207 A | 1/1996 | Mahawili | |
| 5,507,792 A * | 4/1996 | Mason et al. | 607/104 |
| 5,647,051 A | 7/1997 | Neer | |
| 5,806,335 A * | 9/1998 | Herbert et al. | 62/434 |
| 5,848,701 A * | 12/1998 | Riccabona | 206/702 |
| 5,865,841 A | 2/1999 | Kolen et al. | |
| 5,888,185 A * | 3/1999 | Regan | 600/15 |
| 5,895,418 A | 4/1999 | Saringer | |
| 5,948,012 A | 9/1999 | Mahaffey et al. | |
| 6,026,978 A * | 2/2000 | Clegg et al. | 220/592.1 |
| 6,086,609 A | 7/2000 | Buckley | |
| 6,176,869 B1 | 1/2001 | Mason et al. | |
| 6,551,348 B1 | 4/2003 | Blalock et al. | |
| 6,736,309 B1 | 5/2004 | Westerman et al. | |
| 6,837,420 B2 | 1/2005 | Westerman et al. | |
| 6,962,600 B2 | 11/2005 | Lennox et al. | |
| 6,968,955 B2 * | 11/2005 | Steeber | 206/702 |
| 7,052,509 B2 | 5/2006 | Lennox | |
| 7,122,763 B1 * | 10/2006 | Liu et al. | 219/214 |
| 7,347,327 B2 | 3/2008 | Lobman | |
| 2007/0045152 A1 * | 3/2007 | Kwok et al. | 206/733 |
| 2007/0118194 A1 * | 5/2007 | Mason et al. | 607/104 |
| 2007/0187416 A1 | 8/2007 | Maxson | |
| 2007/0193999 A1 * | 8/2007 | Peterson et al. | 219/386 |
| 2008/0060374 A1 * | 3/2008 | Gammons et al. | 62/259.3 |
| 2008/0203090 A1 * | 8/2008 | Dickinson | 220/1.5 |

\* cited by examiner

DISPOSABLE PORTABLE THERAPY DEVICE

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of Invention

This invention pertains to a portable thermal therapy system that is disposable. More particularly, this invention pertains to a coolant system for temperature therapy of an animal in which the coolant system is self-contained for shipping and delivery and is adapted for single use.

2. Description of the Related Art

It is advantageous to selectively apply thermal treatment to patients. Hypothermic treatment is useful for emergency treatment of injured persons. A common first aid for sports injuries is to apply ice or cooling to the injured area. Additionally, patients are often prescribed treatment programs involving application of a thermal device to a body portion of the patient periodically over a period extending from days to months. Cooling treatment is also useful for providing comfort. Many menopausal women have found relief from hot flashes by using cooling treatment to quickly lower their body temperature during the onset of a hot flash.

Physicians have used various devices and techniques to cool the body, including pharmacological cooling and various types of mechanically induced cooling. Mechanically induced cooling approaches generally fall into one of three categories: conductive, convective, or evaporative. While different implementations have been tried, many are limited by lack of practicality, difficulty of use, ineffectiveness, and/or excessive power consumption.

Conductive cooling therapy, that is, a cooling treatment in which the heat transfer mechanism is conduction as opposed to radiation or convection, is known and has been used. Ice packs, although primitive, provide quick localized cooling. A disadvantage of ice packs is that it is difficult to control the rate of cooling. It is also known to circulate a cooled fluid through a thermal pad wrapped around an extremity of a person. The fluid is cooled using various techniques, including using a refrigerant to cool the fluid.

A variety of conductive cooling therapy devices are known. An example of one such device is disclosed in Patent Application Publication Number 2008/0060374, published Mar. 13, 2008, titled "Portable coolant system." The portable coolant system includes a hardshell cooler, such as a portable ice chest, with exposed fluid connectors. The configuration of the cooler is such that the cooler and peripheral components must be packaged in another container for shipping and handling in order to avoid damaging the various components and/or the exposed fluid connectors. Further, the hardshell ice chest is made of materials that are intended for extended use and it is not practical and economical to dispose of the portable coolant system after a patient completes a course of therapy.

These types of conductive cooling therapy devices are constructed for durability and are not suited for environmentally friendly disposal. Further, durable devices require components and construction techniques that make the therapy devices expensive, thereby discouraging the disposal of the therapy devices after the course of treatment is completed.

Foldable portable coolers are known. For example, U.S. Pat. No. 6,837,420, titled "Foldable portable cooler with enhanced over-center locking handle," issued on Jan. 4, 2005, discloses a container configured for storing beverage containers. Such foldable portable coolers are passive devices that provide advantages by being shipped and stored as flat blanks in bulk and being conveniently deployed by end users.

BRIEF SUMMARY OF THE INVENTION

According to one embodiment of the present invention, a portable thermal therapy device is provided. The therapy device has a shipping configuration in which the therapy device is self-contained in a lightweight, yet durable container that is suitable for shipping, handling, and storing. After being received by an end user, the therapy device has a deployed configuration in which various components are removed and/or extended from inside the container such that the therapy device is able to be used for treatment of a patient. In this way, the patient conveniently receives a single, preassembled therapy device requiring minimal assembly and setup.

The container includes a box and a lid, with an insert inside the box. The insert has a cavity that is insulated from the environment outside the box. Inside the cavity is a pump that is attached to the floor of the cavity. The outlet of the pump is connected to a thermal pad that is stored inside the cavity when the therapy device is in the shipping configuration. A compartment is defined between the insert and the inside of the box. The compartment receives the electrical cables, power supply, and control unit when the therapy device is in the shipping configuration. In the shipping configuration, the compartment is sealed with a closure. The closure is removed to expose an opening when the therapy device is in the deployed configuration, thereby allowing portions of the electrical components to be removed from the compartment.

In one embodiment, the insert is a solid material with insulation properties, such as Styrofoam. The insulated insert has a cavity divided into two regions. The bottom region is smaller than the upper region. The outside of the insulated insert adjacent the bottom region is dimensioned to fit inside the upper region of another insulated insert, thereby allowing multiple insulated inserts to be nested for shipping before being assembled to make a therapy device. The insulated insert has channels and notches for routing of the electrical cable between the cavity and the compartment and for routing the fluid lines from the cavity to outside the box. The insulated insert cooperates with an insulated cap attached to the inside surface of the lid of the container.

In another embodiment, the insert is formed from a planar sheet into a basket shape that nests inside the box. The shell insert has a cavity defined by sidewalls. The lip of the cavity has spacers, or connectors, with a flap that is attached to the box near the lip of the box. The electrical cable is routed through the space between connectors at an upper inside corner of the box as the cable is routed from the cavity to the space between the shell insert and the box. The cavity has a floor or bottom. The outside surface of the floor has a base extending from the surface to the inside bottom of the box. The base is a spacer that supports the shell insert at the floor.

The shell insert is formed from a planar sheet that is waterproof. In various embodiments the sheet is a waterproof material or at least one surface of the sheet is coated with a waterproof material or a waterproof membrane is proximate at least one surface of the sheet. The sheet has a number of fold lines, such as scores or creases in the sheet, that aid in forming the sheet into a number of planar panels that are joined at the fold lines.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

Apparatus for disposable portable thermal therapy device 100 is disclosed. The device is a compact, self-contained therapeutic device 100 suitable for patients to use in self-directed care. As used herein, the patient is an animal, which includes humans.

Figure 1:
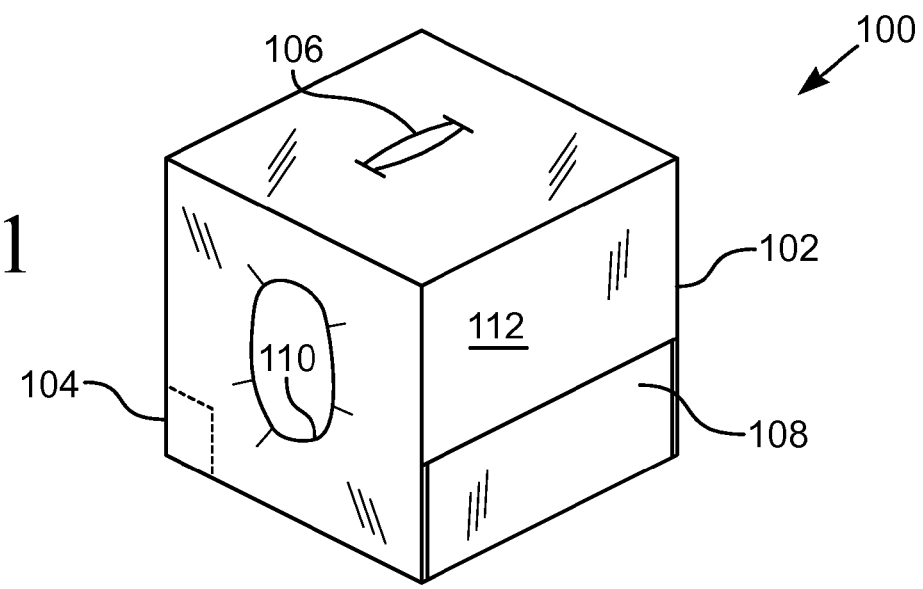
FIG. 1 is a perspective view of one embodiment of a disposable therapy device configured for shipping.

FIG. 1 illustrates a perspective view of one embodiment of a disposable therapy device 100 configured for shipping. The device 100 has a container 102 with a six-sided polygon shape. The illustrated configuration is with the therapy device 100 in a shipping configuration or state. The container 102 is enclosed in a wrap 108, such as a shrink wrap. The wrap 108 encloses the sides of the container 102 except for where the ends of the wrap 108 form an opening 110 on opposite sides of the container 102. For example, a polymer plastic film with a tubular shape sufficiently large enough for the container 102 to fit within is heat shrunk to enclose the container 102 with the ends 110 of the plastic film shrinking to substantially enclose the container 102. In another example, the plastic film is a sheet that is wrapped around the container 102 before heat is applied. In such an application the container 102 may be completely covered with no end openings 110.

In the illustrated embodiment, the container 102 has a handle 106 on the top surface. The illustrated handle 106 is a strap in which the ends fit into slots in the container 102. In one embodiment, the handle 106 is enclosed in the wrap 108 to aid in shipping and handling of the container 102 by avoiding protrusions from the surface of the container 102. In another embodiment, the handle 106 is outside the container 102 to allow the container 102 to be maneuvered by use of the handle 106.

Visible in a lower corner of the container 102 is an opening 104 with a perforated cover. In one such embodiment, the wall of the container 102 has a perforation that, when broken, creates an opening or portal 104 to the interior of the container 102. In other embodiments a removable plug covers the opening 104 until the opening 104 is desired to be used.

The container 102 has planar panels formed from a larger planar sheet that is bent and joined together. In various embodiments, the container 102 is a box fabricated of cardboard or other stiff planar material, such as a plastic or fiberboard. A corrugated material provides strength with light weight, and a solid material, such as pressed fiberboard, provides strength with minimal thickness. The planar material of the container 102 is folded or otherwise shaped to produce the desired configuration of the container 102. The container 102 has a closure 112, shown with the closure 112 sealing the container 102. The construction of the container 102 is such that it is suitable for shipping, handling, and storing the disposable therapy device 100. That is, the container 102 is sufficiently durable to survive the rigors of shipping, handling, and storage without damage to the components inside the container 102.

Figure 2:
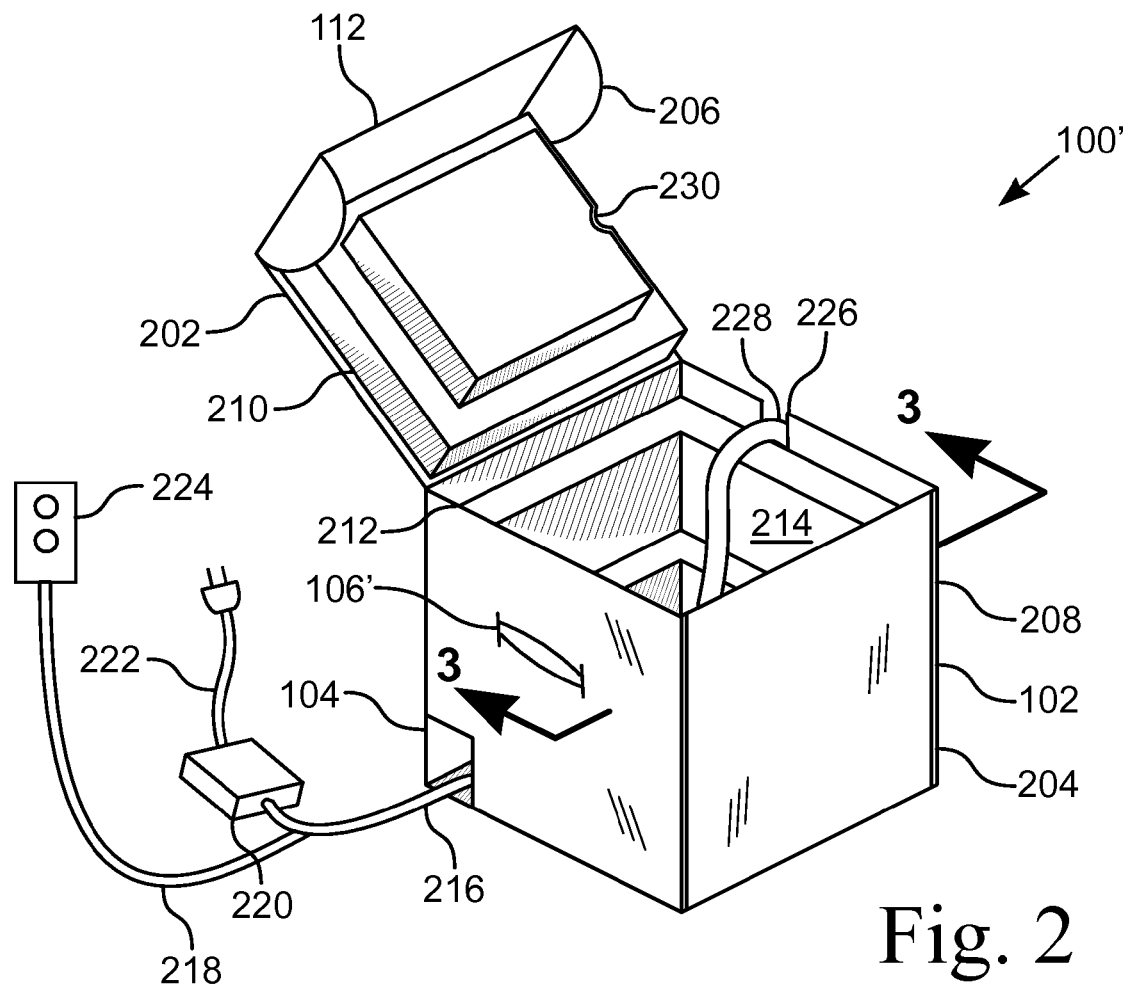
FIG. 2 is a perspective view of a disposable therapy device with various components removed from the container.

FIG. 2 illustrates a perspective view of one embodiment of a disposable therapy device 100' with various components removed from the container 102. In the illustrated embodiment, the device 100' includes a pair of handles 106' disposed on opposite sides of the container 102. The illustrated handle 106' is a strap in which the ends fit into slots in the container 102. In other embodiments, the handles are openings in opposite sides of the container 102, with the openings configured to receive the fingers of a person lifting the device 100'. In yet another embodiment, a strap extending from one side to an opposite side is attached to the container 102 and is suitable for lifting and moving the container 102.

The container 102 includes a lid 202, shown in the open position, and a box 204. The box 204 has four sides, a bottom, and an open top. The top of the box 204 is covered by the lid 202, which includes the closure 112. On the lateral sides of the closure 112 are flaps 206 that fit into slots 208 on either side of the front of the box 204. When the flaps 206 engage the slots 208, the lid 202 is secured to the box 204. In this way, the handle 106 on top of the container 102 is operable to lift the container 102 without the lid 202 inadvertently opening. In another embodiment, the closure 112 is secured to the box 204 by a fastener or clasp. For example, a hook and loop fastener system releasably secures the closure 112 to the outside surface of the box 204, and the hook and loop fastener system has sufficient shear strength to prevent the lid 202 from disengaging the box 204 when a lifting force is applied to the lid 202.

Inside the box 204 is an insulated insert 212 that has a cavity 214. In one embodiment, the cavity 214 has a size sufficient to contain 8 to 10 liters of liquid. Attached to the inside surface of the lid 202 is an insulated cap 210 that engages and covers the opening in the insulated insert 212. When the lid 202 swings down to cover the box 204, the insulated cap 210 is configured to swing into position on top of the insulated insert 212. In one embodiment, the insulated insert 212 and cap 210 are Styrofoam or other material that is suitable for providing temperature isolation between a water-ice mixture in the cavity 214 and the ambient environment outside the container 102.

Visible in a lower corner of the container 102 is the opening 104 in which the perforated cover has been removed. Extending from the opening 104 is a cable 216 connected to a power supply 220, which is connected to a power cable 222 that is configured to connect to a power source, such as a 110Vac wall socket. The power supply 220 converts the power from the power source to a voltage and/or current level that is suitable for use by the portable therapy device 100. In one embodiment, the cable 216 connects directly to a power source and the power supply 220 and power cable 222 are not used. In such an embodiment, the pump 312 and the control unit 224 do not require that the voltage of the power source by converted to another voltage level for use.

The illustrated embodiment shows the cable 216 splitting before connecting to the power supply 220. The split-off control cable 218 has an end connected to a control unit 224. The control cable 218 has a length sufficient for an operator of the therapy device 100 to manipulate the controls on the control unit 224. For example, a patient wearing a pad 302 with the container 102 on the floor is able to operate the control unit 224.

In the illustrated embodiment, the cables 216, 218, the power supply 220 and the power cable 222, and the control unit 224, are removed from the container 102 through the opening 104. In another embodiment, the power supply 220 remains in the container 102 and the power cable 222 extends through the opening 104 along with the control cable 218.

The lip at the top of the box 204 has a slot or opening 226. A sheath 228 extends from the cavity 214 inside the insulated insert 212 through the slot 226. A corresponding notch 230 is formed in the insulated cap 210. The notch 230 provides clearance for the sheath 228 when the lid 202 is closed and the cap 210 engages the insulated insert 212.

Figure 3:
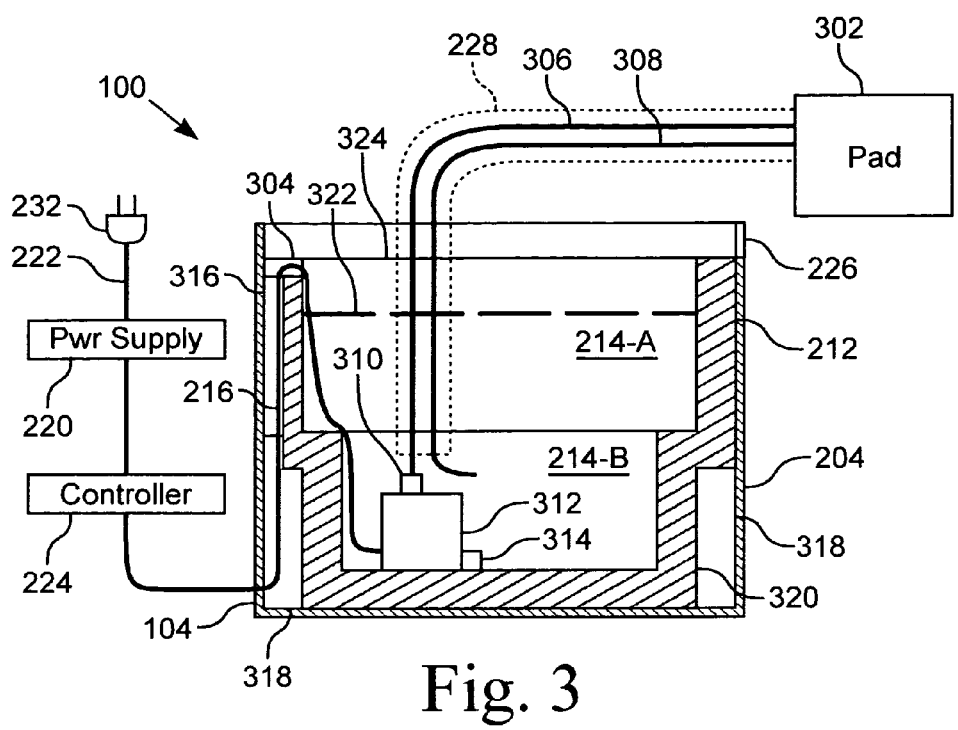
FIG. 3 is a cross-sectional view of one embodiment of a disposable therapy device showing one embodiment of an insulated insert.
Figure 4:
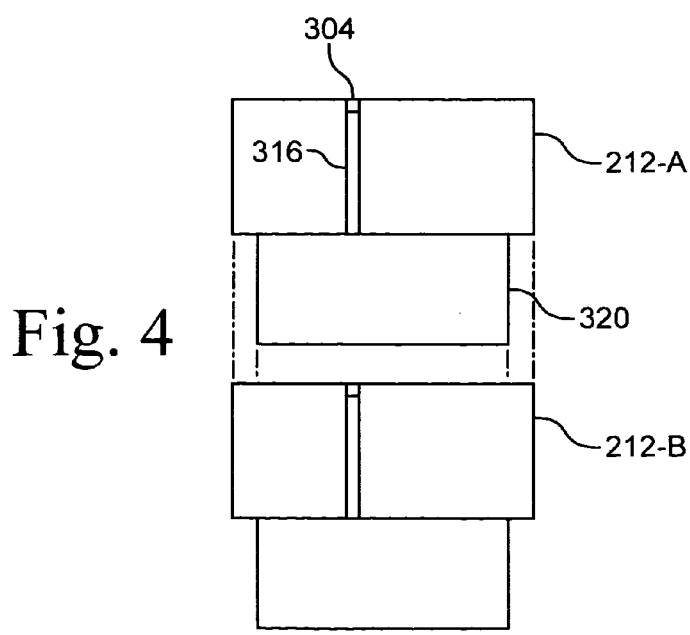
FIG. 4 is a pair of insulated inserts showing their nesting capability.

FIG. 3 illustrates a cross-sectional view of one embodiment of a disposable therapy device 100 showing one embodiment of an insulated insert 212. FIG. 4 illustrates a pair of insulated inserts 212-A, 212-B showing their nesting capability. FIGS. 2 and 3 illustrate the therapy device 100 in the deployed configuration.

Each insulated insert 212 has a first cavity 214-A and a second cavity 214-B. The first cavity 214-A is dimensioned such that the outside surface of the insert 212 has a sliding engagement with the inside surface of the box 204. In this way, the insert 212 is readily positioned inside the box 204, yet rests inside the box with minimal movement relative to the sidewalls of the box 204.

The second cavity 214-B is joined to the first cavity 214-A to define one larger cavity 214. The second cavity 214-B is slightly smaller than the first cavity 214-A. The second cavity 214-B is dimensioned such that the outside surface 320 of a first insulated insert 212-A fits into the first cavity 214-A of a second insulated insert 212-B. The height of the outside surface 320 is approximately equal to the depth of the inside surface of the first cavity 214-A, which ensures that the nested insulated inserts 214-A, 214-B have a minimal height when nested, thereby aiding in minimizing storage and shipping space of the insulated inserts 214-A, 214-B.

The outside surface of one side of the insulated insert 212 adjacent the first cavity 214-A has a groove 316 that connects with a notch, or slot, 304 on the lip 324 of the first cavity 214-A. The cable 216 fits into the groove 316 and the notch 304 when the insulated insert 212 is inside the box 204. That is, the groove 316 and the notch 304 define a passageway for the cable 216 between the inside surface of the box 204 and the insulated insert 212. In another embodiment, the groove 316 and notch 304 are located adjacent a corner of the insulated insert 212.

Inside the second cavity 214-B is a pump 312. In one embodiment the pump 312 is attached to the inside bottom surface of the insulated insert 212, such as by attaching to a bracket fixed to the surface or by attaching the pump 312 directly to the surface, for example, with an adhesive or fasteners. In the illustrated embodiment, the pump 312 is a submersible unit configured to be operated while submerged in a liquid. The pump 312 is an electrically driven device that receives electric power from the cable 216 and operates, when electrically energized, by receiving water from an intake port 314 and discharging that water from an exhaust port 310. In the illustrated embodiment the intake port 314 is separated from the discharge port 310, although in other embodiments the separation varies.

The exhaust port 310 of the pump 312 is connected to a supply line 306 that is connected to the intake of a thermal pad 302. The outlet of the thermal pad 302 is connected to a return line 308 that discharges inside the cavity 214. The supply and return lines 306, 308 are inside the sheath 228, which carries the lines 306, 308 as they are routed from the cavity 214 to the thermal pad 302. The return line 308 is not connected to anything in the illustrated embodiment, but discharges into the cavity 214 directly. In another embodiment, the end of the return line 308 is fixed inside the cavity 214 to anchor the line 308 and to ensure that the warmed water discharged from the return line 308 is directed in a selected manner. In one embodiment, the supply and return lines 306, 308 are joined in a single, integral pair of conduits. As such, the sheath 228 is not necessary to keep the supply and return lines 306, 308 together as they run between the cavity 214 and the pad 302.

The thermal pad 302 is a device that is configured to be positioned adjacent a portion of the patient's body. The thermal pad 302 includes flat pads and shaped pads, both of which include fluid channels that allow the fluid from the supply line 306 to flow through the pad and exit through the return line 308. The therapy pad 302 provides for heat transfer between the patient's body and the fluid flowing from the cavity 214.

The cable 216 is connected to the pump 312 at one end. The cable 216 is routed along the inside surfaces of the insulated insert 212, through the notch 304, along the channel 316 and into the compartment 318. The compartment 318 is the volume between the inside surface of the box 204 and the outside surface 320 of the insulated insert 212. The cable 216 exits the opening 104 in the container 102. FIG. 3 symbolically illustrates the cable 216 connected to the controller, or control unit, 224, which is connected to the power supply 220, which is connected to the power cable 222, which has a connector 232 at its distal end. The power from the power supply 220 is controlled by the control unit 224 to operate the pump 312. In various embodiments the control unit 224 includes controls to energize and de-energize the therapy device 100 and/or a timer for controlling the operating time and/or the duty cycle of the therapy device 100. In another embodiment, the human operated controls, for example the on/off switch, is on a device remote to the control unit 224 and the device is in communication with the control unit 224, such as through a cable or wireless connection As used herein, the control unit 224 should be broadly construed to mean any device that accepts inputs and provides outputs based on the inputs, for example an analog control device, an application specific integrated circuit (ASIC), a microcontroller, or a computer or component thereof that executes software. In various embodiments, the control unit 224 is one of a specialized device or a computer for implementing the functions of the invention. The control unit 224 includes input/output (I/O) units for communicating with external devices and a processing unit that varies the output based on one or more input values. The input component of the control unit 224 receives input from external devices, such as temperature sensors and control button positions, such as those indicating on, off, timer, and duty cycle. The output component sends an output signal to external devices, such as the pump 312.

The disposable therapy device 100 is self-contained and suitable for shipping in the configuration illustrated in FIG. 1. The various components illustrated in FIG. 3 that are shown outside the container 102 are inside for shipping. The cable 216, the controller 224, the power supply 220, and the power cable 222 are stored in the compartment 320. The pump 312, the sheath 228 with the two lines 306, 308, and the thermal pad 302 are stored in the cavity 214. With the opening 104 covered and the lid 202 covering the box 204, the therapy device 100 is self-contained. To aid in preventing damage during shipping, the cavity 214 also contains packing material around the pump 312, the sheath 228, and the pad 302.

Preparing the disposable therapy device 100 for use includes removing the wrap 108 from the container 102. The perforated cover is removed from the opening 104 and the controller 224 and the power cable 222 are removed from the compartment 318 through the opening 104. In one embodiment, the power supply 220 remains inside the compartment 318, as does the cable 216. In another embodiment, the power supply 220 and a portion of the cable 216 are removed from the compartment 318, along with the controller 224 and its cable 218. In yet other embodiments, the cable 216 is connected to the power supply via a connector and/or the controller is connected to the control cable 218 via a connector. The power supply 220 and power cable 222 and/or the controller 224 are then stored in the cavity 214 during shipping and removed and connected to their respective cables 216, 218 when preparing for use.

Preparing the device 100 for use also includes opening the lid 202 and removing the pad 302 and the end of the sheath 228 from the cavity 214. If the pump 312 is not attached to the inside of the insulated insert 212, the pump 312 is secured to a bracket or clip fixed to the inside of the insert 212.

In operation, a user fills the cavity 214 to the fill line 322 with a mixture of water and ice. The ice may be chips, cubes, chunks, or a block. Additives or other substances may also be mixed with the water. The fill line 322 is indicia that indicates an optimum level of fluid in the cavity 214. The user, after ensuring that the controller 224 is in the off position if it has a mechanical type switch, connects the power plug 222 into a power source, such as the 115Vac mains or a battery. The pad 302 is applied to the body portion to be treated. The controller 224 is then operated to cause the fluid in the cavity 214 to flow through the pad 302.

Figure 5:
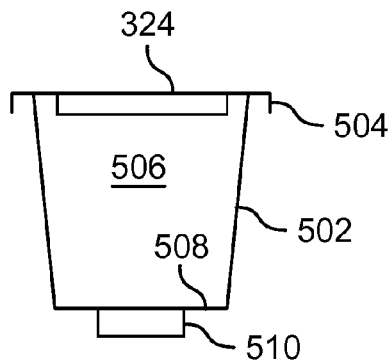
FIG. 5 is a side view of another embodiment of an insert.
Figure 6:
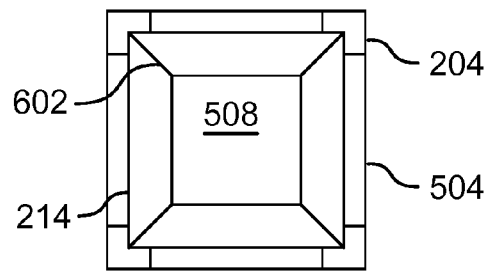
FIG. 6 is a top view of the insert in the cooler box.

FIG. 5 illustrates a side view of another embodiment of an insert 502. FIG. 6 illustrates a top view of the shell insert 502 in the box 204. The shell insert 502 has the general shape of an inverted, truncated 4-sided pyramid, that is, it has a basket shape. The shell insert 502 has four sidewalls 506 and a floor, or bottom, 508. The inside of the shell insert 502 defined by the four sidewalls 506 and the floor, or bottom, 508 is a cavity 214. The sidewalls 506 are separated by a crease 602. Extending from the lip 324 of the shell insert 502 at each sidewall 506 is a connector, or upper spacer, 504. The connector 504 has a flap 702 that attaches to the inside surface of the box 204 to secure the shell insert 502 in the box 204.

Adjacent the floor 508 and on the outside surface of the shell insert 502 is a base 510. The base 510 is a spacer that separates the floor 508 from the inside bottom surface of the box 204. In various embodiments, the bottom base, or spacer, 510 is hollow and has a cylindrical-shape, a polygonal-shape, or other configuration that supports the remainder of the shell insert 502 above the inside bottom of the box 204.

The shell insert 502, in combination with the box 204, forms an insulated cavity 214. The air gap between the inside surfaces of the box 204 and the outside surfaces of the shell insert 502 is an insulator. Conduction is minimized by limiting the contact between the box 204 and the shell insert 502 to only the connectors 504 and the base 510. In another embodiment, insulating material is placed in the air gap between the box 204 and the shell insert 502 except for a volume that defines the compartment 318 for storing the electrical components 216, 222, 218, 224. For example, expanding foam is injected in the upper portion of the volume, leaving the compartment 318 below unobstructed.

Figure 7:
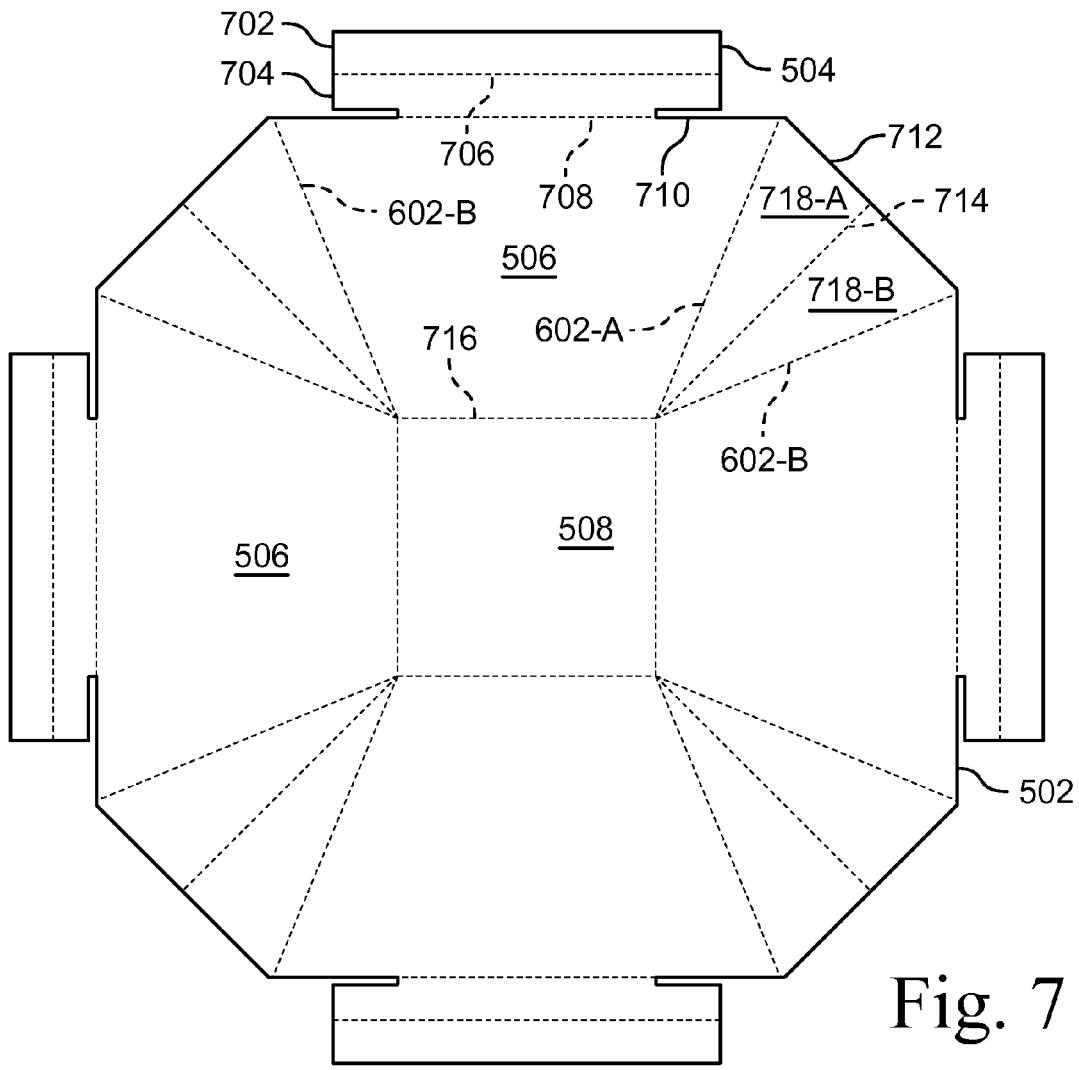
FIG. 7 is a plan view of one embodiment of an insert before it is folded into a basket-shape.
Figure 8:
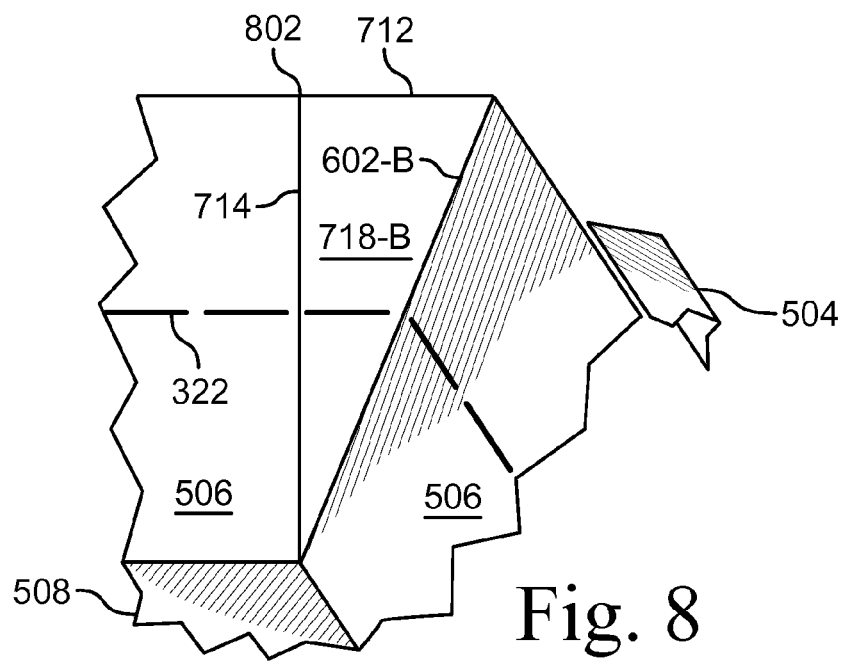
FIG. 8 is a partial inside view of the insert.

FIG. 7 illustrates a plan view of one embodiment of a shell insert 502 before it is folded into a basket-shape. FIG. 8 illustrates a partial inside view of the insert 502. The shell insert 502 in its non-deployed state as shown in FIG. 7, is a planar sheet that is impervious to water and fluids on at least one side.

In various embodiments, the shell insert 502 is fabricated of cardboard or other stiff planar material, such as a plastic or fiberboard. The surface of the shell insert 502 that defines the cavity 214, in one embodiment, is coated with a layer or has a membrane on the surface that is a polymer or other material that is water proof or water-resistant. In its deployed state, the shell insert 502 is watertight such that the insert 502 is able to contain a liquid, such as water, without leakage. The shell insert 502 has fold lines, for example the fold lines 716 that define the floor 508. The fold lines, in one embodiment, are scores or creases in the planar material that create weakened areas that allow the planar material of the shell insert 502 to fold into two intersecting panels at the fold line. The planar material of the shell insert 502 is folded or otherwise shaped to produce the desired configuration of the shell insert 502.

The connectors 504 of the shell insert 502 have a flap 702 that is outboard of an extension 704. The flap 702 is separated from the extension 704 by a fold line 706 that allows the flap 702 to be positioned at an angle to the extension 704. The flap 702 has a surface area that is sufficient to attach to the inside surface of the box 204, such as with an adhesive or a fastener. The extension 704 is separated from the sidewall 506 by a fold line 708 that allows the extension 704 to be positioned at an angle relative to the sidewall 506. The extension 704 is not connected to the sidewall 506 along the full length of the extension 704, but is also separated from the sidewall 506 by a pair of slots 710. The slots 710 minimize the conduction from the cavity 214 to the box 204 and the length of the fold line 708 is sufficient to provide enough mechanical strength to support the shell insert 502 in the box 204.

In another embodiment, the connectors, or spacers, 504 have three panels, or flaps, having a substantially U-shape. One panel, or flap, 702 is attached to an inside surface of the box 204, the middle panel 704 bridges the gap between the inside surface of the box 204 and the lip 324, and the third panel is attached to a sidewall panel 506 adjacent the lip 314. In yet another embodiment, the connector 504 is a spacer that separates the box 204 from the lip 324 while physically connecting the two 204, 324. In these ways, the connectors, or spacers, 504 functions similarly to the connector 504 illustrated in FIG. 7, which shows the connectors 504 being unitary with the insert 502.

The sidewalls 506 are defined by four fold lines 708, 602-A, 602-B, 716. Adjacent to and between pairs of sidewalls 506 are a pair of corner panels 718-A, 718-B. The two corner panels 718-A, 718-B are separated by a fold line 714. The opposite edge of each corner panel 718-A, 718-B is separated from its adjacent sidewall panel 506 by a fold line 602-A, 602-B.

To form the basket shape of the shell insert 502, the two corner panels 718-A, 718-B are brought together such that the fold line 714 protrudes into the cavity 214 being formed. At the same time, each of the fold lines 716 between the sidewall panels 506 and the bottom panel 508 define the apex of the two panels 506, 508 as the material of the insert 502 is bent. One corner panel 718-A is brought adjacent a sidewall panel 506 and laid flat against the inside surface of a sidewall 506 as illustrated in FIG. 8. The corner 802 formed by the juncture of the center fold line 714 and the edge 712 between the connectors 504 is in-line with the lip 324 of the cavity 214, which is where the fold line 708 between the sidewall 506 and the extension 704 is located. Accordingly, the cavity 214 is waterproof up to the lip 324.

In another embodiment, there is only one corner panel 718-B that is attached to a sidewall panel 506. There is a wedge-shaped gap between the corner panel 718-B and the other adjacent sidewall panel 506. The corner panel 718-B is a flap that is then adhesively attached to the other adjacent sidewall panel 506. For example, the inside surface of the other adjacent sidewall panel 506 is adhered to the corresponding surface of the corner panel 718-B with the adhesively joined joint forming a water-tight seal between the adjacent sidewall panels 506. In another embodiment, the cavity 214 is lined with a layer that is water tight.

Figure 9:
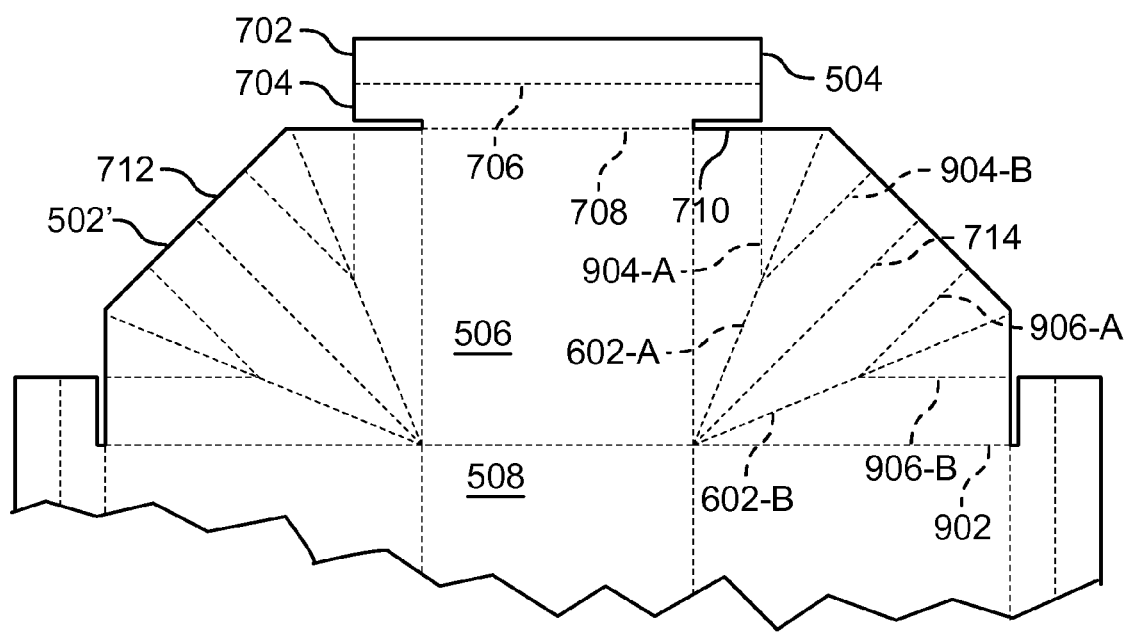
FIG. 9 is a partial plan view of another embodiment of an insert before it is folded into a basket-shape.

FIG. 9 illustrates a partial plan view of another embodiment of an insert 502' before it is folded into a basket-shape. The illustrated embodiment is similar to that illustrated in FIG. 7, with the addition of additional fold lines 902, 904-A, 904-B, 906-A, 906-B. The additional fold lines 904-A, 904-B, 906-A, 906-B allow the corners of the shell insert 502' between the sidewalls 506 to more closely conform to the corners of the box 204, thereby increasing the volume contained by the cavity 214.

The disposable therapy device 100 includes various functions. The function of controlling the flow of fluid through the pad 302 is implemented, in one embodiment, by the control unit 224 that is operatively connected to the pump 312 to turn the pump 312 on and off based on operation of a manual control and/or by operation of a timer circuit that switches the power to the pump 312.

The function of minimizing thermal transfer between the ambient environment outside the container 102 and the contents of the cavity 214 is implemented, in one embodiment, by the insulated insert 212, which is a material with low thermal conductivity, such as Styrofoam. In another embodiment, the function of minimizing thermal transfer is implemented by a shell insert 502 inside a box 204 with an air gap between the two 502, 204. In such an embodiment, the physical connection between the shell insert 502 and the box 204 is only large enough to provide the necessary structural integrity to support the shell insert 502 in the box 204. In one such embodiment, the air gap is filled with an insulating material that has a lower thermal transfer rate than air.

The function of supplying temperature controlled fluid to a thermal pad 302 is implemented, in one embodiment, by a pump 312. In one embodiment, the pump 312 is submergible and secured to the bottom 508 of a cavity 214 that is filled with a fluid.

The function of providing a therapy device 100 that is disposable is implemented, in one embodiment, by fabricating the device 100 with a minimum of non-biodegradable materials. In one such embodiment, the container 102 and the shell insert 502, which make the bulk of the material of the device 100, are biodegradable materials, such as cardboard.

The function of routing a cable 216 from the pump 312 in the cavity 214 to the compartment 318 between the insert 212, 502 and the box 204 is implemented, in one embodiment, by the channel 316 and the notch 304 in the insulated insert 212. In another embodiment, the cable 216 is routed through the space between adjacent connectors 504 near the upper inside corner of the box 204.

The function of ensuring that the cavity is waterproof and is capable of holding a quantity of liquid is implemented, in one embodiment, by folding a planar sheet into the basket shape of the shell insert 502, with the surface of the shell insert 502 that defines the cavity 214 being waterproof. For example, in various embodiments the planer sheet is waterproof, the surface of the sheet is coated or otherwise treated to make it waterproof, or a waterproof liner is positioned inside the cavity 214 adjacent the surface of the cavity 214.

From the foregoing description, it will be recognized by those skilled in the art that a disposable therapy device 100 has been provided. The device 100 is a self-contained therapy device that is fabricated of materials that are readily disposable, but sufficiently strong and durable to survive a course of treatment that may last several months.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. An apparatus for a thermal therapy device, said apparatus comprising:
    a container having a box and a lid, said lid being releasably securable to said box;
    an insert having a cavity defined by an inside surface of said insert, said inside surface of said insert being waterproof, said insert configured to contain a volume of water, said insert substantially filling an inside volume of said box, said insert being a thermal insulator suitable for providing temperature isolation between a water-ice mixture in said cavity and an ambient environment outside said container;
    an insulator attached to said lid of said container, said insulator engaging an opening of said cavity when said lid is in a closed position;
    a compartment defined by an inside surface of said box and an outside surface of said insert, said compartment configured to have an opening through a side of said box;
    a pump having an outlet port and an inlet port, said pump secured inside said cavity proximate said bottom of said box;
    a cable connected to said pump, said cable providing electrical power to said pump;
    a thermal pad connected to said outlet port of said pump through a first conduit, said thermal pad configured to be positioned adjacent a body portion of a patient, said thermal pad connected to a second conduit having a distal end discharging into said cavity;
    a control unit operatively connected to said pump;
    a power connection providing power to said control unit and said pump;
    said container having a first configuration in which said lid is closed, said thermal pad and said first and second conduits are inside said cavity, said control unit is inside said container, and said cable is stored inside said compartment, wherein said first configuration is suitable for shipping said apparatus without requiring said container to be inserted into a shipping container; and
    said container having a second configuration wherein said cable extends from said opening in said box and said first and second conduits extend from said cavity to said pad, which is outside said box, wherein said apparatus is configured to be used by the patient.

2. The apparatus of claim 1 further including a film wrapped around said container when said container is in said first configuration, and said film substantially enclosing said container.

3. The apparatus of claim 1 wherein said insert defines a passageway in which said cable is routed from said pump in said cavity to said compartment between said insert and said box.

4. The apparatus of claim 1 wherein said cavity of said insert has a first cavity section and a second cavity section; said second cavity section defined by a first plurality of sidewalls; and said first cavity section dimensioned to receive a second plurality of sidewalls having the same configuration and dimensions as said first plurality of sidewalls wherein another insert is nestable with said insert.

5. The apparatus of claim 1 wherein said first configuration of said container presents a plurality of panels defining said container as a plurality of planar surfaces free of any protrusions, wherein said container when in said first configuration is suitable for shipping.

6. The apparatus of claim 1 wherein said insert defines a single cavity extending from a lip of said insert to an inside bottom surface of said insert, and said inside bottom surface of said insert is positioned proximate a bottom of said box.

7. An apparatus for a thermal therapy device, said apparatus comprising:
a container with a plurality of panels defining a lid and a box, said plurality of panels being rigid and planar, said lid being releasably securable to said box when said lid is in a closed position, said container having a passageway bounded by said box and said lid when said lid is in said closed position, said passageway configured to receive a conduit without interfering with said lid when said lid is in said closed position;
an insert inside said box, said insert having thermal insulating properties suitable for providing temperature isolation between an outside surface and an inside surface of said insert when said inside surface contains a water-ice mixture, said inside surface defining a cavity, said cavity configured to contain a liquid, said insert having a first section and a second section, said first section being below said second section when said cavity is oriented to contain the liquid, said second section of said insert having a channel extending between a top of said insert to said first section, and said channel proximate said outside surface;
an insulator attached to said lid of said container, said insulator engaging an opening of said cavity when said lid is in said closed position;
a compartment defined by said outside surface of said insert proximate said first section and an inside surface of said box, said box configured to have an opening into said compartment;
a pump having an outlet port and an inlet port, said pump secured inside said cavity proximate said bottom of said box, said passageway in said container configured to allow the conduit to pass from the pump to outside said container when said lid is in said closed position; and
a first cable connected to said pump, said first cable providing electrical power to said pump, said first cable passing through said channel in said second section of said insert, said compartment configured and dimensioned to temporarily store a distal end of said first cable inside said compartment.

8. The apparatus of claim 7 wherein said outside surface proximate said first section is dimensioned to fit within said second section whereby said insert, when not inside said box, is configured to be stacked as one of a plurality of inserts.

9. The apparatus of claim 7 further including a controller and a power cable, said compartment configured and dimensioned to temporarily store said controller and said power cable inside said compartment.

10. The apparatus of claim 9 further including a power supply electrically connected to said power cable, and said compartment configured and dimensioned to temporarily store said power supply, said controller, and said power cable inside said compartment.

11. The apparatus of claim 7 further including a thermal pad and said conduit connecting said thermal pad to said pump, said conduit passing through said passageway when said lid is in said closed position.

12. An apparatus for a thermal therapy device, said apparatus comprising:
a container having a rectangular shape with a plurality of sides, a lid, and a bottom, said lid hingedly connected to one of said plurality of sides;
an insert inside said container, said insert extending from a top of said to container to said bottom, said insert defining a cavity configured to contain a liquid, said insert being a closed cell foam with a thickness sufficient to provide temperature isolation between a water-ice mixture in said cavity and an ambient environment outside said container;
a cap attached to a bottom surface of said lid, said cap engaging a top opening of said insert when said lid is in a closed position, said cap being a closed cell foam insulator;
a compartment proximate said bottom of said container between said insert and at least one of said plurality of sides of said container;
an opening into said compartment, said opening in one of said plurality of sides of said container;
a channel extending from said top opening of said insert to said compartment, said channel defined by said insert and one of said plurality of sides of said container;
a pump in said cavity, said pump proximate said bottom of said box;
a cable connected to said pump, said cable extending up from said pump to said channel, said cable extending through said channel to said compartment;
a thermal pad configured to be positioned adjacent a body portion of a patient;
a first conduit connected to said pump and to said thermal pad; and
a second conduit connected to said thermal pad and discharging into said cavity.

13. The apparatus of claim 12 further including a closure attached to a distal edge of said lid, said closure being a planar panel, said closure including a pair of flaps on opposite edges of said closure, and said pair of flaps configured to engage corresponding slots in said box.

14. The apparatus of claim 12 wherein said cavity is an unobstructed open volume in said insert, said cavity extends from a lip of said insert to an inside bottom surface of said insert, and said inside bottom surface of said insert is positioned proximate a bottom of said box.

15. The apparatus of claim 12 wherein said container has a shipping configuration in which said lid is in said closed position, a distal end of said cable is contained in said compartment, said thermal pad and said first and second conduits are stowed in said cavity, and an outside of said container presents a plurality of planar surfaces free of any protrusions.

16. The apparatus of claim 12 wherein said container has a deployed configuration wherein said cable extends from said opening in said compartment and said first and second conduits extend from said cavity to said thermal pad located outside said container.

17. The apparatus of claim 12 wherein said insert has an upper section and a lower section, said upper section having a sliding engagement with an inside surface of said plurality of sides of said container, and said compartment being a space between said lower section and an inside of said box proximate said bottom.

18. The apparatus of claim 17 wherein an inside of said upper section is dimensioned to receive an object that is dimensioned identically to said lower section of said insert, whereby multiple inserts are nestable when said multiple inserts are separated from corresponding multiple containers.

19. The apparatus of claim 12 wherein said container has a conduit passageway between said box and lid, said conduit passageway configured to receive said first and second conduits when said lid is in said closed position.

20. An apparatus for a thermal therapy device, said apparatus comprising:
a container having a box and a lid, said box having an opening in a side wall proximate a bottom of said box;
an insert defining a cavity that is configured to contain a liquid, said cavity being an unobstructed open volume in said insert, said insert being a closed cell foam with a thickness sufficient to provide temperature isolation between a water-ice mixture in said cavity and an ambient environment outside said container,
said insert having an upper section defined by a plurality of upper sidewalls, opposing ones of said plurality of upper sidewalls being parallel, said upper section being dimensioned to have a sliding engagement with an inside surface of said container, said upper section having a channel defined by an outside surface of one of said plurality of upper sidewalls and said inside surface of said container, said channel extending from a top of said upper section to said lower section,
said insert having a lower section defined by a plurality of lower sidewalls, opposing ones of said plurality of lower sidewalls being parallel, said lower section being dimensioned to define a compartment between an outside surface of at least one of said plurality of lower sidewalls and said inside surface of said container;
a cap attached to a bottom surface of said lid, said cap engaging a top opening of said insert when said lid is in a closed position;
a pump positioned inside said insert proximate said bottom of said box, said pump having a cable routed from the pump, through the inside of said insert, through the passageway in said upper section of said insert, and into said compartment; and
said container has a shipping configuration wherein said shipping configuration has said lid in said closed position with a distal end of said cable stored in said compartment, and an outside of said container presents a plurality of planar surfaces free of any protrusions.

21. The apparatus of claim 20 further including a thermal pad configured to be positioned adjacent a body portion of a patient; a first conduit connected to said pump and to said thermal pad; and a second conduit connected to said thermal pad and discharging into said cavity.

22. The apparatus of claim 21 wherein said cavity is dimensioned to store said thermal pad and said first and second conduits when said lid is closed.

23. The apparatus of claim 21 wherein a conduit passageway is defined between said lid and an upper edge of said box whereby when said lid is in said closed position said first and second conduits extend from said cavity through said conduit passageway.

24. The apparatus of claim 20 wherein said cap being a closed cell foam insulator.

25. The apparatus of claim 20 further including a controller and a power cable, said compartment configured and dimensioned to store said controller and said power cable inside said compartment when said container is in said shipping configuration.

26. The apparatus of claim 25 further including a power supply electrically connected to said power cable, and said compartment configured and dimensioned to store said power supply, said controller, and said power cable inside said compartment when said container is in said shipping configuration.

* * * * *